United States Patent
Shimohata (10) Patent No.: US 10,327,335 B2
(45) Date of Patent: Jun. 18, 2019

(54) CONNECTION STRUCTURE AND IMAGE PICKUP APPARATUS

(71) Applicant: OLYMPUS CORPORATION, Tokyo (JP)

(72) Inventor: Takahiro Shimohata, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/782,987

(22) Filed: Oct. 13, 2017

(65) Prior Publication Data

US 2018/0042109 A1 Feb. 8, 2018

Related U.S. Application Data

(63) Continuation of application No. PCT/JP2015/061430, filed on Apr. 14, 2015.

(51) Int. Cl.
*H05K 1/11* (2006.01)
*H05K 1/14* (2006.01)
(Continued)

(52) U.S. Cl.
CPC ......... *H05K 1/144* (2013.01); *A61B 1/00124* (2013.01); *A61B 1/041* (2013.01);
(Continued)

(58) Field of Classification Search
CPC ............ H05K 1/141–144; H05K 1/181; H01L 2924/01078–01079; H01L 2924/1627; H01L 2924/0013; H01L 2924/13099
(Continued)

(56) References Cited

U.S. PATENT DOCUMENTS 7,745,923 B2 * 6/2010 Hirose .............. H01L 27/14618
257/698
9,167,686 B2 * 10/2015 Chen .................. H01L 23/3121
(Continued)

FOREIGN PATENT DOCUMENTS

JP     H05-152706 A     6/1993
JP     2000-199863 A    7/2000
(Continued)

OTHER PUBLICATIONS

International Search Report dated Jun. 23, 2015 received in PCT/JP2015/061430.

*Primary Examiner* — Tuan T Dinh
(74) *Attorney, Agent, or Firm* — Scully, Scott, Murphy & Presser, P.C.

(57) ABSTRACT

A connection structure includes: a wiring board including a plurality of first electrodes that are arranged on a principal surface; a molded interconnect device (MID) made of a non-electroconductive resin as a base material, the MID including a side surface and a bottom surface, the bottom surface being parallel to the principal surface of the wiring board and including a plurality of arranged second electrodes, and the side surface being perpendicular to the principal surface of the wiring board; and a plurality of electroconductive members each made of an electroconductive paste, each of the electroconductive members electrically connecting each of the plurality of first electrodes to each of the plurality of second electrodes, in which the plurality of electroconductive members are housed in respective reservoir sections formed by the second member and are not in contact with the non-electroconductive resin.

11 Claims, 6 Drawing Sheets

(51) Int. Cl.
*A61B 1/00* (2006.01)
*A61B 1/04* (2006.01)
*H01L 27/146* (2006.01)

(52) U.S. Cl.
CPC .............. *H05K 1/111* (2013.01); *H05K 1/119* (2013.01); *H01L 27/14618* (2013.01); *H01L 27/14636* (2013.01); *H05K 2201/041* (2013.01); *H05K 2201/09027* (2013.01); *H05K 2201/09072* (2013.01); *H05K 2201/09118* (2013.01); *H05K 2201/09381* (2013.01); *H05K 2201/10121* (2013.01); *H05K 2201/10151* (2013.01); *H05K 2203/0465* (2013.01)

(58) Field of Classification Search
USPC .................................. 361/767–777, 790, 803
See application file for complete search history.

(56) References Cited

U.S. PATENT DOCUMENTS

2008/0099236 A1  5/2008  Cayaban et al.
2011/0317386 A1  12/2011  Kawabata

FOREIGN PATENT DOCUMENTS

| | | |
|---|---|---|
| JP | 2004-120000 A | 4/2004 |
| JP | 2004-248753 A | 9/2004 |
| JP | 2005-006769 A | 1/2005 |
| JP | 2006-173152 A | 6/2006 |
| JP | 2006-237276 A | 9/2006 |
| JP | 2007-036481 A | 2/2007 |
| JP | 2008-166471 A | 7/2008 |
| JP | 2010-507923 A | 3/2010 |
| WO | 2008/051602 A2 | 5/2008 |
| WO | 2010/106601 A1 | 9/2010 |

* cited by examiner

CONNECTION STRUCTURE AND IMAGE PICKUP APPARATUS

CROSS REFERENCE TO RELATED APPLICATION

This application is a continuation application of PCT/JP2015/061430 filed on Apr. 14, 2015, the entire contents of which are incorporated herein by this reference.

BACKGROUND OF THE INVENTION

1. Field of the Invention

The present invention relates to a connection structure in which a first member and a second member that is a molded interconnect device are electrically connected to each other through electroconductive members each made of an electroconductive paste, and to an image pickup apparatus including the connection structure.

2. Description of the Related Art

A molded interconnect device (MID) is a three-dimensional device in which electroconductive patterns are provided on an injection molded product. For example, Japanese Patent Application Laid-Open Publication No. 2004-248753 discloses a capsule medical device in which the MID is electrically connected to a wiring board and the like through solder bonding.

Using an electroconductive paste makes it possible to electrically connect the MID to the wiring board at low temperature.

SUMMARY OF THE INVENTION

A connection structure according to an embodiment of the present invention includes: a first member including a plurality of first electrodes that are arranged on a principal surface; a second member that is a molded interconnect device made of a non-electroconductive resin as a base material, the second member including a side surface and a bottom surface, the bottom surface being parallel to the principal surface of the first member and including a plurality of arranged second electrodes, and the side surface being perpendicular to the principal surface of the first member and including a plurality of arranged wirings respectively extended from the plurality of second electrodes; and a plurality of electroconductive members each made of an electroconductive paste, each of the electroconductive members electrically connecting each of the plurality of first electrodes to each of the plurality of second electrodes, in which the plurality of electroconductive members are housed in respective reservoir sections formed by the second member and are not in contact with the non-electroconductive resin. An image pickup apparatus according to another embodiment includes a connection structure inside a housing, and the connection structure includes: a first member including a plurality of first electrodes that are arranged on a principal surface; a second member that is a molded interconnect device made of a non-electroconductive resin as a base material, the second member including a side surface and a bottom surface, the bottom surface being parallel to the principal surface of the first member and including a plurality of arranged second electrodes, and the side surface being perpendicular to the principal surface of the first member and including a plurality of arranged wirings respectively extended from the plurality of second electrodes; and a plurality of electroconductive members each made of an electroconductive paste, each of the electroconductive members electrically connecting each of the plurality of first electrodes to each of the plurality of second electrodes, in which the plurality of electroconductive members are housed in respective reservoir sections formed by the second member and are not in contact with the non-electroconductive resin.

DETAILED DESCRIPTION OF THE PREFERRED EMBODIMENTS

<First Embodiment>

Figure 1:
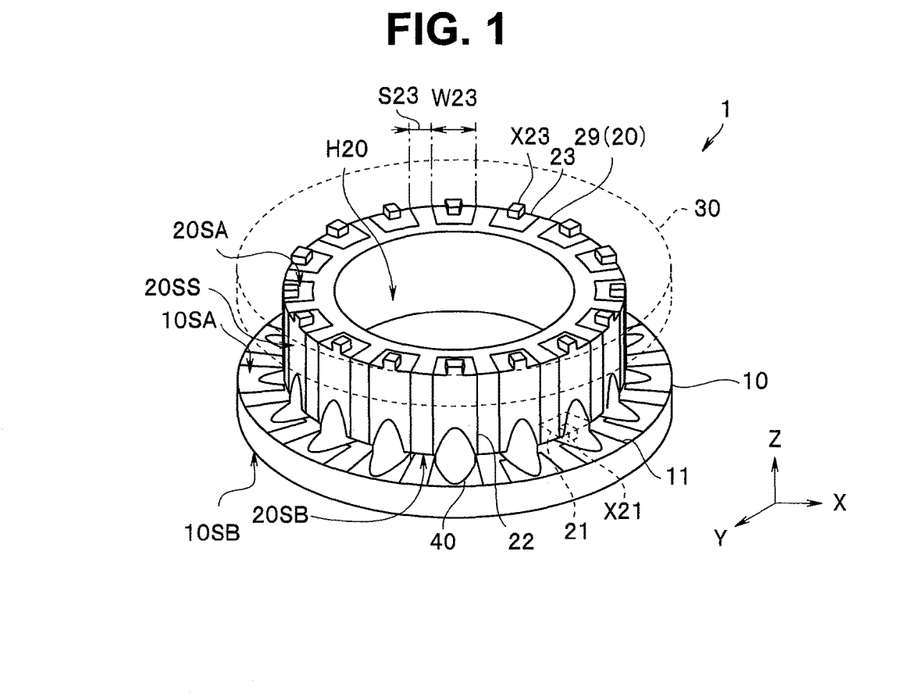
FIG. 1 is a perspective view illustrating a connection structure according to a first embodiment.

As illustrated in FIG. 1, a connection structure 1 according to an embodiment of the present invention is a three-dimensional wiring board that includes a wiring board 10 serving as a first member, a molded interconnect device (MID) 20 serving as a second member, and electroconductive members 40 each made of an electroconductive paste. A wiring board 30 serving as a third member that has a configuration substantially same as a configuration of the wiring board 10 is bonded to an upper surface of the MID 20.

Note that, in the following description, drawings based on respective embodiments are conceptual sketches and may not reflect actual relationship between a thickness and a width of each portion, actual proportion of the thickness of each portion, etc. Dimensional relationships and proportions may also differ from one drawing to another. In addition, a direction in which a value of a Z axis increases is referred to as an upward direction.

A plurality of first electrodes 11 are concentrically arranged on a principal surface 10SA of the circular wiring board 10. Although not illustrated, electronic devices such as an image pickup device, a light emitting diode, and a chip capacitor are mounted on a principal surface 10SB opposite to the principal surface 10SA. The first electrodes 11 are electrically connected to the electronic devices through, for example, a through-hole wiring.

The cylindrical MID 20 is disposed such that a side surface 20SS is perpendicular to the principal surface 10SA of the wiring board 10, and a bottom surface 20SB is parallel to the principal surface 10SA of the wiring board 10. A plurality of second electrodes 21 are concentrically arranged on the bottom surface 20SB. Wirings 22 that are extended from the respective second electrodes 21 are arranged on the side surface 20SS. Third electrodes 23 that are extended from the respective wirings 22 are arranged on a top surface of the cylindrical MID 20.

A base material 29 of the MID 20 is a non-electroconductive resin, in particular, moldable engineering plastic. The base material 29 is made of, for example, polyamide (PA), polycarbonate (PC), liquid crystal polymer (LCP), polyether ether ketone (PEEK), nylon, polyphthalamide (PPA), acrylonitrile-butadiene-styrene resin (ABS), or a material in which an inorganic filler is added to any of these materials.

An electroconductive pattern such as the electrode 21 of the MID 20 is fabricated through a laser removing method, a pattern plating method, or the like. In the laser removing method, a conductive film is formed on an entire surface of a molded product through a plating method or the like, and an unnecessary portion is then removed through laser irradiation. In the pattern plating method, a mask pattern is disposed on the surface of the molded product, and a plating film is formed on a region not covered with the mask. Further, a plating film may be formed only in a region provided with a catalyst layer of electroless plating by patterning the catalyst layer.

The electroconductive pattern is made of a low electric resistance material such as gold and copper, and may have a single-layered or a multilayered underlayer made of titanium, chromium, nickel, or the like in order to improve adhesiveness.

The electroconductive paste that contains the low electric-resistance metal particles, a binder, and a solvent is dried and solidified, thereby becoming the electroconductive member 40. The metal particles are made of at least one kind of metal selected from, for example, nickel, gold, silver, copper, aluminum, and iron. Examples of the binder may include an ethyl cellulose resin, a nitro cellulose resin, an acrylic resin, an alkyd resin, or a combination of the resins. As the solvent, α-terpineol, xylene, toluene, diethylene glycol monobutyl ether, diethylene glycol monobutyl ether acetate, diethylene glycol monoethyl ether, diethylene glycol monoethyl ether acetate, and the like are singularly or mixedly used.

Note that the content of the electroconductive powder in the electroconductive paste is not particularly limited; however, 70 wt % to 90 wt % is normally preferable and 75 wt % to 85 wt % is particularly preferable.

If the solvent of the electroconductive paste evaporates at room temperature or at low temperature equal to or lower than 100° C., the electroconductive paste becomes a solid that is the low-resistance electroconductive member 40.

The respective electroconductive members 40 electrically connect and bond the second electrodes 21 of the MID 20 to the first electrodes 11 of the wiring board 10 concurrently. Likewise, the third electrodes 23 on the top surface of the MID 20 are also electrically connected to the third electrodes (not illustrated) of the wiring board 30 by the respective electroconductive members 40.

Note that the wiring board 10 and the MID 20 may be bonded by a non-electroconductive adhesive, and the electroconductive paste may be then applied to dispose the electroconductive members 40.

Figure 2A:
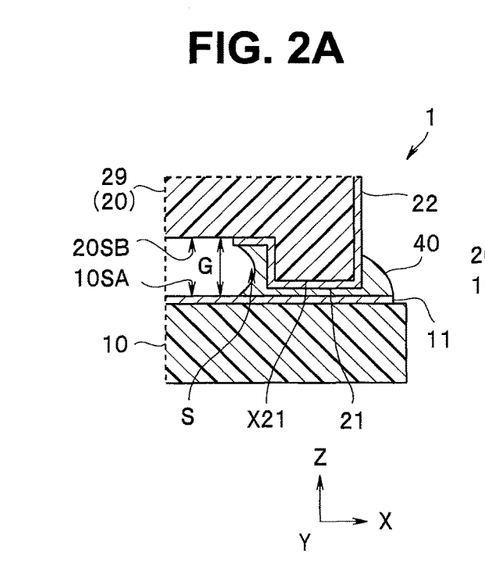
FIG. 2A is a cross-sectional diagram illustrating the connection structure according to the first embodiment.
Figure 2B:
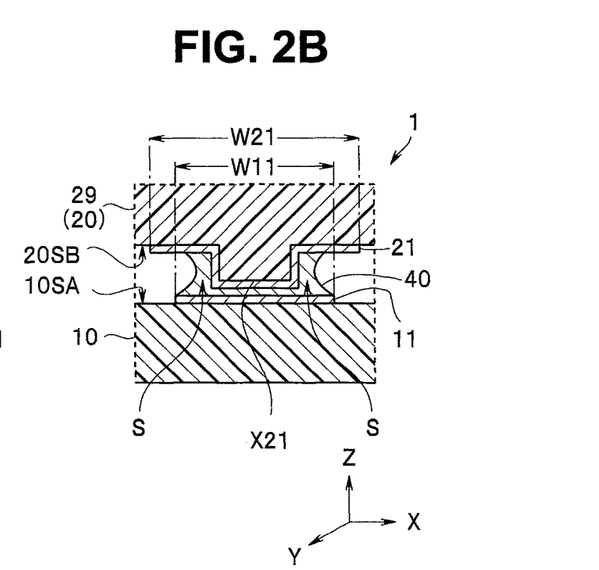
FIG. 2B is a cross-sectional diagram illustrating the connection structure according to the first embodiment.

As illustrated in FIG. 2A and FIG. 2B, a plurality of convex parts X21 each having a height G are provided on the bottom surface 20SB of the MID 20 of the connection structure 1, and convex parts X23 are provided on the top surface 20SA. The convex parts may be molded concurrently with the base material 29 or convex parts made of a material different from the base material 29 may be disposed on the MID 20.

Bonding between the MID 20 and the wiring board 10 is substantially same as bonding between the MID 20 and the wiring board 30. Therefore, the bonding between the MID 20 and the wiring board 10 is described below.

The plurality of second electrodes 21 respectively cover each of the plurality of convex parts X21. In other words, the second electrodes 21 are disposed on a top surface and a side surface of the respective convex parts X21. Note that, in a case where outside surfaces of the respective convex parts X21 and the side surface 20SS of the MID are located on the same plane, the second electrodes 21 and the wirings 22 are formed at the same time, and the respective boundaries between the second electrodes 21 and the wirings 22 are not clear.

In the connection structure 1, a space S is formed between the principal surface 10SA of the wiring board 10 and the bottom surface 20SB of the MID 20 by the convex parts X21. The space S configured by the surfaces of the first electrodes 11 and the surfaces of the second electrodes 21 becomes a reservoir section (reservoir) for the electroconductive paste (the liquid electroconductive member 40). Each of the electroconductive members 40 is housed in the space S serving as the reservoir section that is formed by each of the convex parts X21 of the MID 20. Therefore, the electroconductive members 40 are small in spread and do not come into contact with the non-electroconductive resin of the base material 29 of the MID 20.

Note that making a width W21 of each of the second electrodes 21 larger than a width W11 of each of the first electrodes 11 more surely prevents each of the electroconductive members 40 from spreading around each of the second electrodes 21. For example, in particular, the widths preferably satisfy W21≥W11×2.

The electroconductive members 40 each made of the electroconductive paste are high in bonding strength to a metal but are not high in bonding strength to a resin. For example, bonding strength of the electroconductive member to the base material 29 is equal to or lower than 50% of bonding strength of the electroconductive member to the second electrode 21. Here, the bonding strength is a value measured through 90° peel test (JIS C5016: room temperature, peeling rate: 50 mm/min).

If the electroconductive member 40 on the base material 29 is peeled from the base material 29, even the electroconductive member 40 on the metal electrode may be peeled with the peeled part as a starting point.

In addition, if the electroconductive paste spreads, short-circuit may occur between adjacent electrodes. In particular, in a case where an electrode surface of the MID is in contact with an electrode surface of the wiring board, the electroconductive paste easily spreads along a clearance between the electrode surfaces by interfacial tension.

If an application quantity of the electroconductive paste is decreased or an electroconductive paste with high viscosity is used in order to avoid short-circuit, the connection may become insufficient.

Therefore, the connection structure in which the wiring board is connected to the MID through the electroconductive members each made of the electroconductive paste and the image pickup apparatus including such a connection structure may become low in reliability.

In the connection structure 1 according to the embodiment, however, the electroconductive paste stays on the surface of each of the second electrodes 21, and does not stride over the region from which the base material 29 is exposed. The connection structure 1 having no possibility that even the electroconductive members 40 on the second electrodes 21 are peeled with the upper part of the base material 29 as a starting point, is high in connection reliability between the wiring board 10 and the MID 20.

Note that the connection structure 1 according to the embodiment includes the wiring board 10, the MID 20, and the electroconductive members 40 as the essential components but the wiring board 30 is not an essential component.

In addition, the wiring board 10 and the MID 20 each have a circular shape in a planar view; however, each may have a rectangular shape, a polygonal shape, or the like. Further, the MID 20 has a doughnut shape with a hollow center part; however, may have a columnar shape, a prism shape, a polygonal prism shape, or the like. Furthermore, the MID 20 may have a hollow shape with a bottomed center part.

In addition, as with the connection structure 1, in the MID 20 having the doughnut shape with the hollow center part, the wirings 22 may be disposed on an outer peripheral part as with the MID 20, may be disposed on an inner peripheral part, or may be disposed on both of the outer peripheral part and the inner peripheral part.

<Modifications of First Embodiment>

Next, connection structures 1A to 1A3 according to respective modifications of the first embodiment are described. Each of the connection structures 1A to 1A3 is similar to the connection structure 1 and has effects same as the effects of the connection structure 1. Therefore, a component having the same function described above is denoted by the same reference numeral and description of the component is omitted.

Figure 3A:
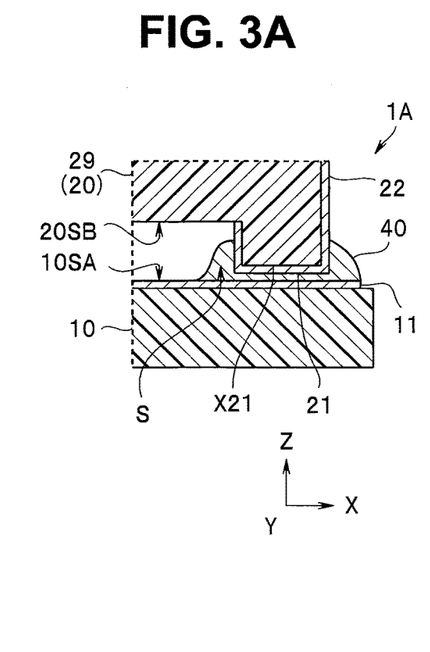
FIG. 3A is a cross-sectional diagram illustrating a connection structure according to a modification of the first embodiment.
Figure 3B:
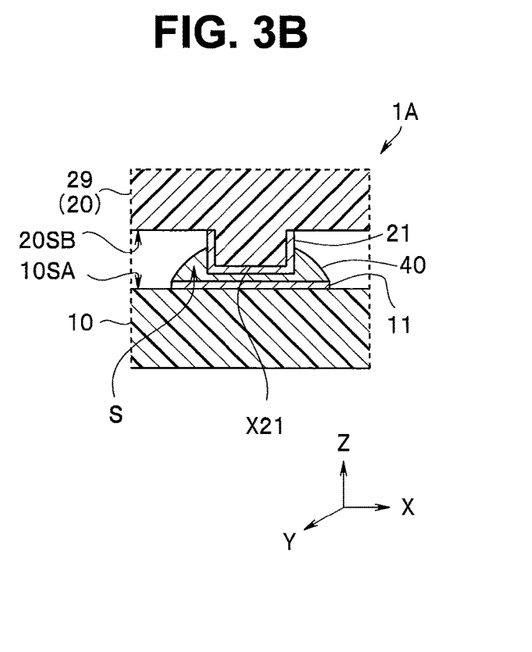
FIG. 3B is a cross-sectional diagram illustrating the connection structure of the modification of the first embodiment.

In the connection structure 1A according to the modification of the first embodiment illustrated in FIG. 3A and FIG. 3B, the number of the electroconductive members 40 is small. Therefore, the electroconductive paste stays on a wall surface of each of the convex parts X21 of the MID 20. Accordingly, it is sufficient to provide the second electrode 21 only on the wall surface of each of the convex parts X21.

Figure 4A:
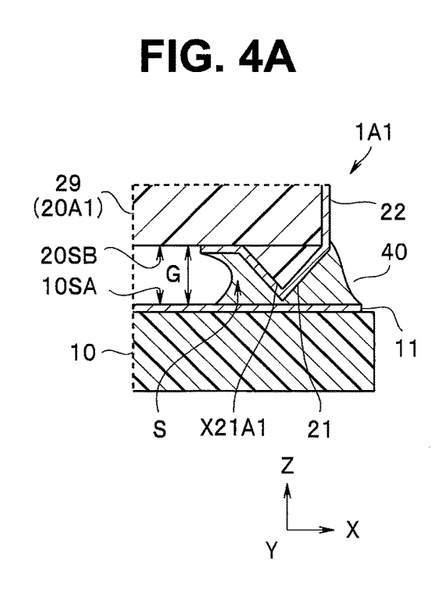
FIG. 4A is a cross-sectional diagram illustrating a connection structure of a modification of the first embodiment.
Figure 4B:
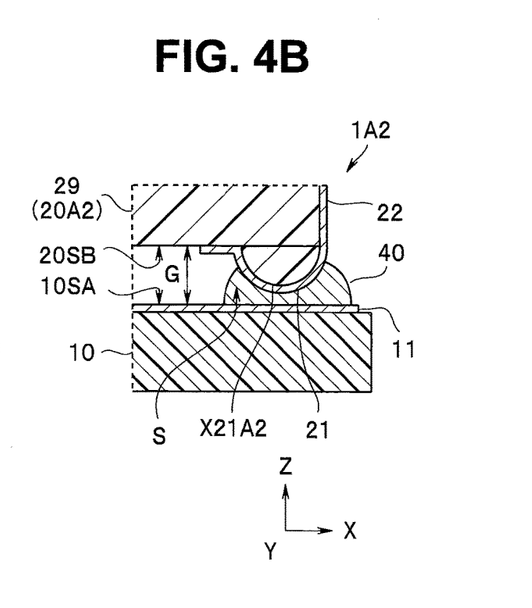
FIG. 4B is a cross-sectional diagram illustrating a connection structure of a modification of the first embodiment.

Further, the cross-sectional shape of each of the convex parts on the bottom surface 20SB of the MID 20 may be a conical shape as with a convex part X21A1 of an MID 20A1 of the connection structure 1A1 illustrated in FIG. 4A, or a substantially hemispherical shape as with a convex part X21A2 of an MID 20A2 of the connection structure 1A2 illustrated in FIG. 4B as long as the convex part forms the space S.

Figure 5A:
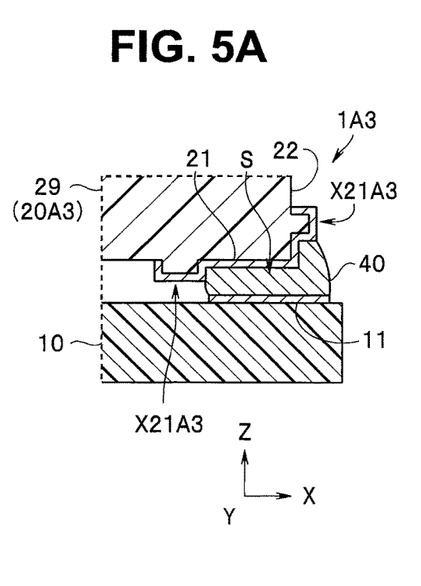
FIG. 5A is a cross-sectional diagram illustrating a connection structure of a modification of the first embodiment.
Figure 5B:
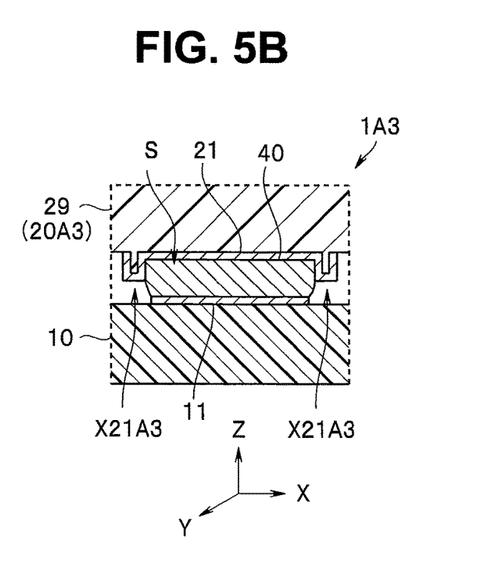
FIG. 5B is a cross-sectional diagram illustrating a connection structure of a modification of the first embodiment.

Furthermore, as with the connection structure 1A3 illustrated in FIG. 5A and FIG. 5B, a frame convex part X21A3 may be provided on the outside of the region, of the MID 20A3, facing the first electrodes 11. The frame convex part X21A3 prevents the electroconductive members 40 from spreading.

<Second Embodiment>

Next, a connection structure 1B according to a second embodiment is described. The connection structure 1B is similar to the connection structure 1 and has effects same as the effects of the connection structure 1. Therefore, a component having the same function described above is denoted by the same reference numeral and description of the component is omitted.

Figure 6A:
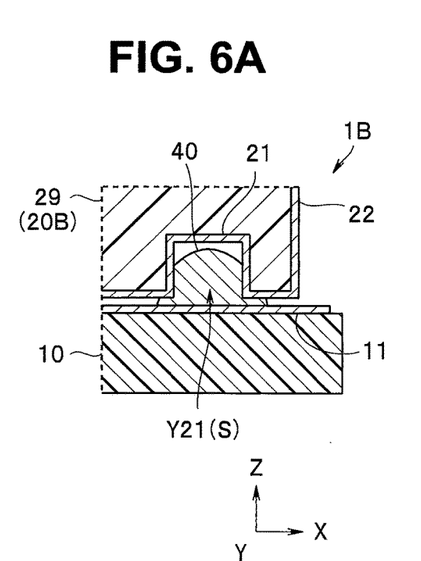
FIG. 6A is a cross-sectional diagram illustrating a connection structure according to a second embodiment.
Figure 6B:
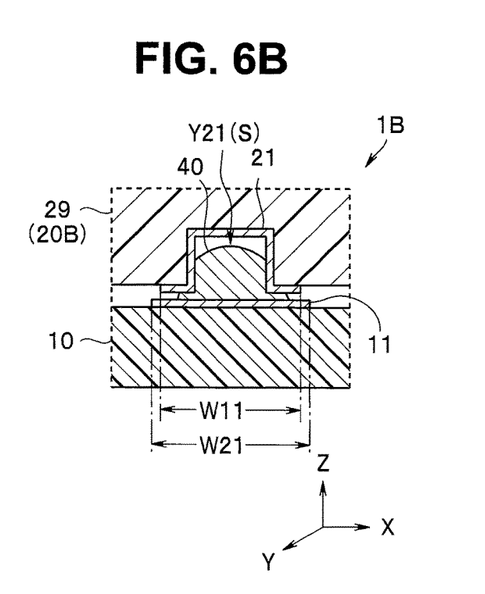
FIG. 6B is a cross-sectional diagram illustrating the connection structure according to the second embodiment.

As illustrated in FIG. 6A and FIG. 6B, in the connection structure 1B, a plurality of concave parts Y21 are provided on the bottom surface 20SB of an MID 20B serving as the second member. Further, the second electrodes 21 respectively cover inner surfaces of the concave parts Y21. The electroconductive members 40 are respectively housed inside the concave parts Y21.

The space S that is formed by each of the concave parts Y21 and is configured by the surface of each of the first electrodes 11 and the surface of each of the second electrodes 21 serves as a reservoir section (a housing portion) that houses excessive electroconductive member 40. Therefore, the electroconductive members 40 are small in spread, and are not in contact with the non-electroconductive resin of the base material 29 of the MID 20B.

As a result, the connection structure 1B is high in connection reliability between the wiring board 10 and the MID 20B.

Note that, as with the connection structure 1, making the width W21 of each of the second electrodes 21 larger than the width W11 of each of the first electrodes 11 more surely prevents each of the electroconductive members 40 from spreading around each of the second electrodes 21. For example, in particular, the widths preferably satisfy $W21 \geq W11 \times 2$.

<Modifications of Second Embodiment>

Next, connection structures 1B1 to 1B3 according to respective modifications of the second embodiment are described. Each of the connection structures 1B1 to 1B3 is similar to the connection structure B1 and has effects same as the effects of the connection structure B1. Therefore, a component having the same function described above is denoted by the same reference numeral and description of the component is omitted.

Figure 7A:
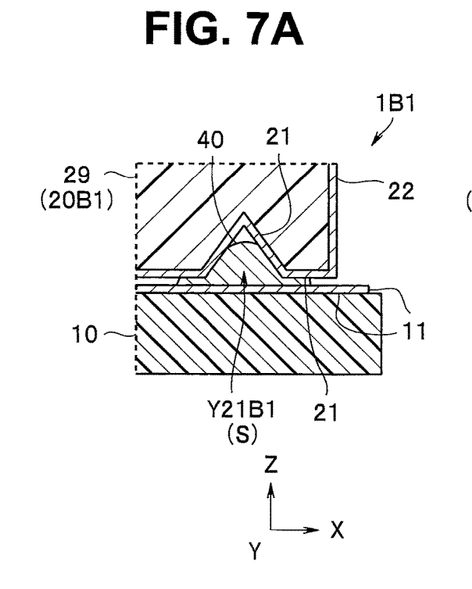
FIG. 7A is a cross-sectional diagram illustrating a connection structure according to a modification of the second embodiment.
Figure 7B:
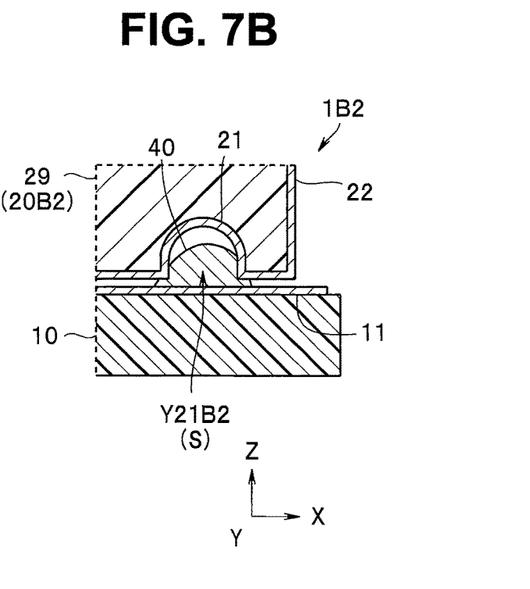
FIG. 7B is a cross-sectional diagram illustrating a connection structure according to a modification of the second embodiment.

In the connection structure 1B1 according to a modification 1 of the second embodiment illustrated in FIG. 7A, the space of a concave part Y21B1 of an MID 20B1 has a conical shape. In the connection structure 1B2 according to a modification 2 illustrated in FIG. 7B, the space of a concave part Y21B2 of an MID 20B2 has a substantially semispherical shape or the like.

Figure 8A:
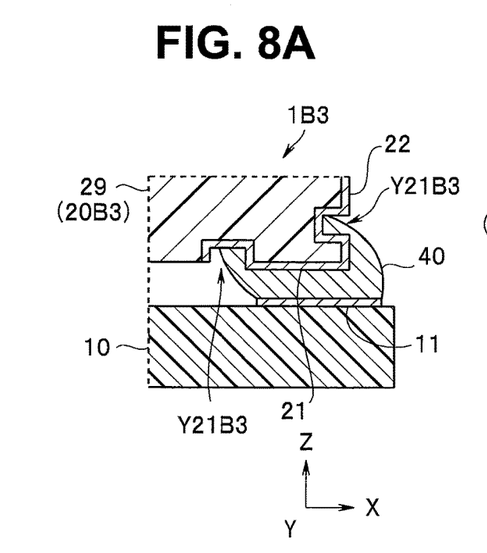
FIG. 8A is a cross-sectional diagram illustrating a connection structure according to a modification of the second embodiment.
Figure 8B:
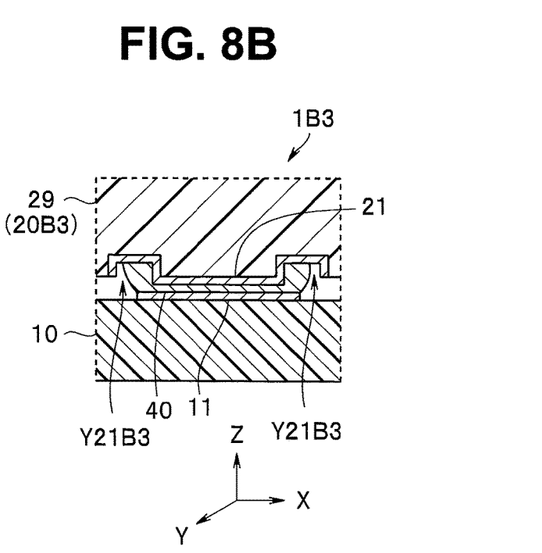
FIG. 8B is a cross-sectional diagram illustrating a connection structure according to a modification 2 of the second embodiment.

Moreover, in the connection structure 1B3 according to a modification 3 illustrated in FIG. 8A and FIG. 8B, a trench serving as a continuous concave part Y21B3 is provided on outside of the region, of the MID 20B3, facing the first electrodes 11. The trench prevents the electroconductive members 40 from spreading.

<Third Embodiment>

Next, a connection structure 1C according to a third embodiment is described. The connection structure 1C is similar to any of the connection structures 1, 1A, and 1B. Therefore, a component having the same function described above is denoted by the same reference numeral and description of the component is omitted.

Figure 9:
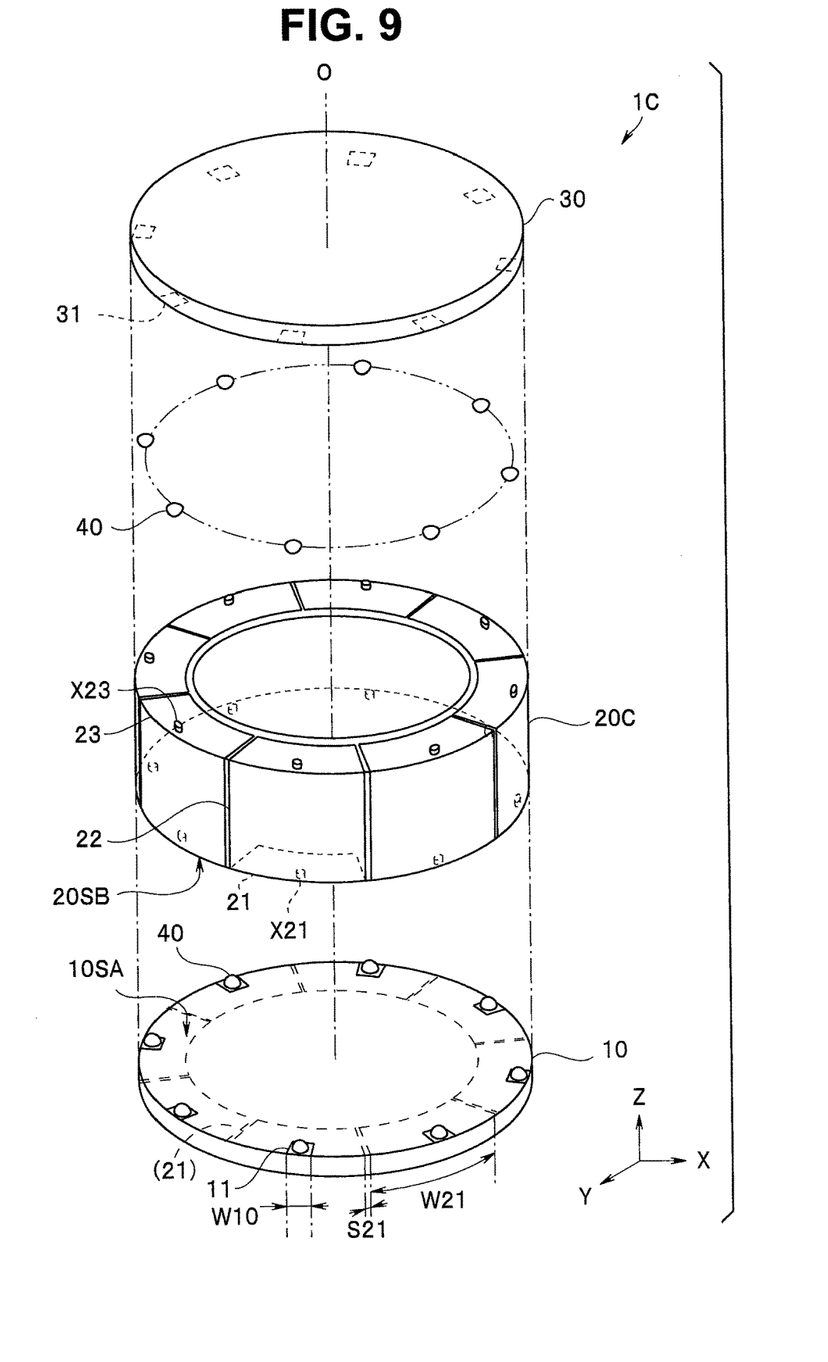
FIG. 9 is an exposed perspective view of a connection structure according to a third embodiment.

In the connection structure 1C illustrated in FIG. 9, electroconductive patterns such as the electrodes 21 of an MID 20C are fabricated through, for example, the laser removing method. In other words, a conductive film is formed over an entire surface of a molded product through a plating method or the like, and an unnecessary portion is then removed through laser irradiation.

At this time, in the connection structure 1C, a slit is provided in order to prevent short-circuit from occurring between adjacent electroconductive patterns. A width S21 of the slit is sufficiently smaller than the width W21 of each of the electrodes 21 and the like, and for example, S21≤0.1× W21 is established. Therefore, most of the surface (the bottom surface 20SB) of the MID 20C bonded to the wiring board 10 is covered with the electrodes 21, and an exposed area of the base material 29 made of a non-electroconductive resin is small.

Further, the width W11 of each of the first electrodes 11 of the wiring board 10 is equal to or lower than 50% of the width W21 of each of the second electrodes 21. Furthermore, the first electrodes 11 are located inside the respective second electrodes 21 as transparently viewed from a direction (the Z direction) orthogonal to the principal surface 10SA of the wiring board 10.

In the connection structure 1C, the electroconductive members 40 have no possibility of coming into contact with the non-electroconductive resin of the base material 29 of the MID 20C. Therefore, the connection structure 1C is high in connection reliability between the wiring board 10 and the MID 20C.

Note that, in the connection structure 1C, all of the wiring board 10, the MID 20C, and the wiring board 30 have a circular shape, the same diameter, and are coincident in center axis with one another. Since the connection structure 1C also has a small diameter, the connection structure 1C is particularly suitable to be built in a capsule housing as described later.

Figure 10A:
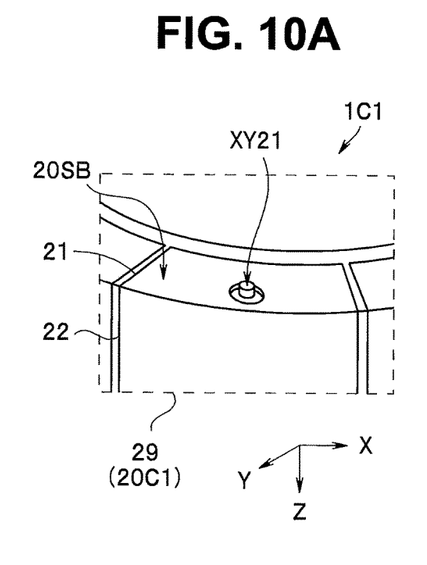
FIG. 10A is a partial perspective view of a connection structure according to a modification of the third embodiment.
Figure 10B:
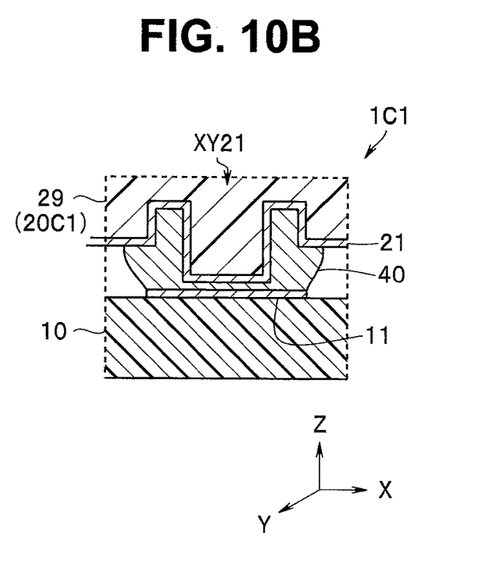
FIG. 10B is a cross-sectional diagram of the connection structure of the modification of the third embodiment.

In addition, the MID 20C includes the convex parts X21 and X23 on the surface bonded to the wiring board 10 as with the MID 20; however, the MID 20C may include concave parts in place of the convex parts, as with the MID 20B. Further, as with an MID 20C1 of a connection structure 1C1 illustrated in FIG. 10A and FIG. 10B, concave-convex parts XY21 each configured of a convex part and a concave part may be provided.

<Fourth Embodiment>

Next, an image pickup apparatus 2 according to a fourth embodiment is described. The image pickup apparatus 2 has a configuration similar to the configuration of any of the connection structures 1 and 1A to 1C as described above. Therefore, a component having the same function described above is denoted by the same reference numeral and description of the component is omitted.

Figure 11:
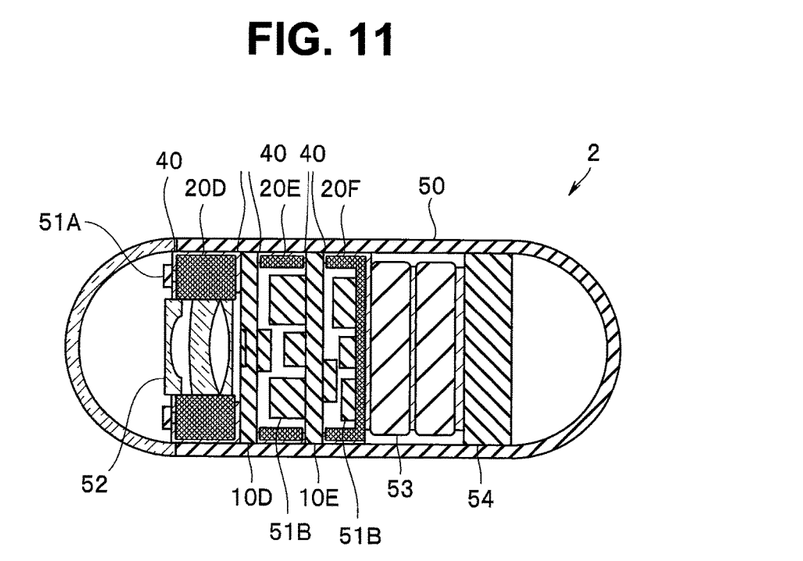
FIG. 11 is a cross-sectional schematic diagram illustrating an image pickup apparatus according to a fourth embodiment.

The image pickup apparatus 2 is a capsule medical device that includes a capsule housing 50 and a three-dimensional wiring board housed inside the housing 50. The three-dimensional wiring board of the image pickup apparatus 2 includes a plurality of MIDs 20D to 20F, and a plurality of wiring boards 10D and 10E. As described later, the wiring board 10D is an image pickup device made of silicon.

The MIDs 20D and 20E each have the configuration substantially same as the configuration of any of the MIDs 20 to 20C. The MID 20F has a hollow shape with a bottomed center part.

An optical system 52 including a plurality of lenses is disposed in a hollow part of the MID 20D. In addition, an LED 51A that is an electronic device is mounted on a top surface of the MID 20D.

The LED 51A and the MID 20D are electrically connected to each other through the electroconductive members 40 each made of the electroconductive paste. In other words, the LED 51A that is the electronic device is regarded as a first member in which a plurality of first electrodes (external electrodes) are arranged on a principal surface.

Second electrodes that are electrically connected to the respective external electrodes are disposed on the top surface of the MID 20D. Further, the second electrodes respectively cover the convex parts or the concave parts. Therefore, also in a bonding part between the electronic device and the MID, each of the electroconductive members 40 made of the electroconductive paste is small in spread, and is not in contact with the non-electroconductive resin of the base material.

An image pickup device 10D provided with a light receiving section is electrically connected to the MID 20D through the electroconductive members 40, which causes the image pickup device 10D to be regarded as the wiring board 10D made of silicon. The wiring board 10E is a double-sided wiring board on which an electronic device 51B is mounted on each of the surfaces. A battery 53 supplying driving power and a spacer 54 are also housed inside the housing 50.

The MID 20D is bonded to a top surface of the image pickup device 10D through the electroconductive members 40 each made of the electroconductive paste, and the MID 20E is bonded to the bottom surface of the image pickup device 10D through the electroconductive members 40. The MID 20E is bonded to a top surface of the wiring board 10E through the electroconductive members 40, and the MID 20F is bonded to the bottom surface of the wiring board 10E through the electroconductive members 40.

In each of the MIDs and the wiring boards (the image pickup device), the electroconductive members 40 are not in contact with the non-electroconductive resin of the base material of the MID, as with the MID 20, the wiring board 10, and the like described above.

Therefore, the image pickup apparatus 2 has no possibility that the electroconductive member 40 is peeled with the upper part of the base material as a starting point, and the image pickup apparatus 2 is accordingly high in reliability.

The present invention is not limited to the embodiments, the modifications, and the like described above, and various modifications, combinations, and applications may be made without departing from the scope of the invention.

What is claimed is:

1. A connection structure, comprising:
   a first member including a first principle surface and a second principal surface opposite to the first principal surface, a plurality of first electrodes being arranged on the first principal surface and electronic devices being mounted on the second principal surface by solder;
   a second member that is a molded interconnect device formed of a non-electroconductive resin as a base material, the second member including a side surface and a bottom surface, the bottom surface being parallel to the first principal surface of the first member and including a plurality of arranged second electrodes, and the side surface being perpendicular to the first principal surface of the first member and including a plurality of arranged wirings respectively extended from the plurality of second electrodes; and a plurality of electroconductive members each made of an electroconductive paste, each of the electroconductive members electrically connecting each of the plurality of first electrodes to each of the plurality of second electrodes, wherein the plurality of electroconductive members are housed in respective reservoir sections formed by the second member and are not in contact with the non-electroconductive resin.

2. The connection structure according to claim 1, wherein the bottom surface of the second member is provided with
a plurality of convex parts,
each of the plurality of second electrodes covers a top surface and a side surface of each of the plurality of convex parts, and
each of the reservoir sections is a space configured of a surface of each of the first electrodes and a surface of each of the second electrodes.

3. The connection structure according to claim 1, wherein the bottom surface of the second member is provided with
a plurality of concave parts,
each of the plurality of second electrodes covers an inner surface of each of the plurality of concave parts,
each of the plurality of electroconductive members is housed inside each of the plurality of concave parts, and
each of the reservoir sections is a space configured of a surface of each of the first electrodes and a surface of each of the second electrodes.

4. The connection structure according to claim 1, wherein each of the plurality of first electrodes is located inside each of the plurality of second electrodes as transparently viewed from a direction orthogonal to the first principal surface of the first member.

5. The connection structure according to claim 1, wherein each of the plurality of second electrodes has a width larger than a width of a space between the adjacent second electrodes.

6. The connection structure according to claim 1, wherein the first principal surface of the first member has a circular shape, and
the second member has a cylindrical shape.

7. The connection structure according to claim 1, wherein the plurality of first electrodes are concentrically arranged on the first principal surface of the first member, and
the plurality of second electrodes are concentrically arranged on the bottom surface of the second member.

8. The connection structure according to claim 1, wherein a solvent included in the electroconductive paste evaporates below a melting temperature of the solder and the electroconductive paste is solidified to become the electroconductive members.

9. The connection structure according to claim 5, wherein the plurality of second electrodes are insulated from one another by a slit that is provided on a conductive film configuring the plurality of second electrodes.

10. An image pickup apparatus comprising;
a connection structure disposed inside a housing, the connection structure comprising:
a first member including a first principal surface and a second principal surface opposite to the first principal surface, a plurality of first electrodes being arranged on the first principal surface and electronic devices being mounted on the second principal surface by solder;
a second member that is a molded interconnect device made of a non-electroconductive resin as a base material, the second member including a side surface and a bottom surface the bottom surface being parallel to the first principal surface of the first member and including a plurality of arranged second electrodes, and the side surface being perpendicular to the first principal surface of the first member and including a plurality of arranged wirings respectively extended from the plurality of second electrodes; and
a plurality of electroconductive members each made of an electroconductive paste, each of the electroconductive members electrically connecting each of the plurality of first electrodes to each of the plurality of second electrodes,
wherein the plurality of electroconductive members are housed in respective reservoir sections formed by the second member and are not in contact with the non-electroconductive resin.

11. The image pickup apparatus according to claim 10, wherein a solvent included in the electroconductive paste evaporates below a melting temperature of the solder and the electroconductive paste is solidified to become the electroconductive members.

* * * * *